(12) United States Patent
Jansen-Troy et al.

(10) Patent No.: US 11,553,927 B2
(45) Date of Patent: Jan. 17, 2023

(54) SURGICAL SAW APPARATUS

(71) Applicant: SMC Innovation GmbH, Cham (CH)

(72) Inventors: Arne Jansen-Troy, Stockach (DE);
Armin Studer, Cham (CH)

(73) Assignee: SMC INNOVATION GMBH, Cham (CH)

(*) Notice: Subject to any disclaimer, the term of this patent is extended or adjusted under 35 U.S.C. 154(b) by 0 days.

(21) Appl. No.: 17/261,911

(22) PCT Filed: Jul. 25, 2018

(86) PCT No.: PCT/CH2018/000032
§ 371 (c)(1),
(2) Date: Jan. 21, 2021

(87) PCT Pub. No.: WO2020/019086
PCT Pub. Date: Jan. 30, 2020

(65) Prior Publication Data
US 2021/0251637 A1  Aug. 19, 2021

(51) Int. Cl.
A61B 17/14 (2006.01)
(52) U.S. Cl.
CPC .......... A61B 17/142 (2016.11); A61B 17/144 (2016.11); A61B 17/147 (2016.11)
(58) Field of Classification Search
CPC .................. A61B 17/142; A61B 17/144
See application file for complete search history.

(56) References Cited

U.S. PATENT DOCUMENTS 2,138,862 A * 12/1938 Johnston ................ B23D 51/16
                                                          74/44
3,640,280 A *  2/1972 Slanker ................ A61B 17/144
                                                          30/392
(Continued)

FOREIGN PATENT DOCUMENTS

DE       8706162 U1      7/1987
DE    102009048835 A1    4/2011
WO     2011/162736 A1   12/2011

OTHER PUBLICATIONS

International Search Report dated Apr. 16, 2019 issued in corresponding International Patent Application No. PCT/CH2018/000032.

(Continued)

Primary Examiner — Nicholas W Woodall
(74) Attorney, Agent, or Firm — Posz Law Group, PLC

(57) ABSTRACT

A surgical saw apparatus, includes: A) a housing; B) a drive unit with a drive axle having a central axis; C) a deflection device, including: a connecting rod that is arranged movably in the housing, with a longitudinal axis, with a rear section and with a front section with members for a fixation of a sawblade; an eccentric shaft with at least one first section, which is arranged coaxially with the central axis of the drive axle and is connected with the drive axle, and with a second section which is eccentric relative to the first section, wherein the rear section of the connecting rod is a bearing for the eccentric second section of the eccentric shaft, and the front section of the connecting rod is a fixation device for a sawblade; and a guiding device for the connecting rod, wherein D) the guiding device includes first members for a limitation of a movement of the connecting rod, which are movable relative to the housing and which force a translational movement of the connecting rod coaxially with the longitudinal axis of the connecting rod, and E) the guiding (Continued)

US 11,553,927 B2

Figure 1:
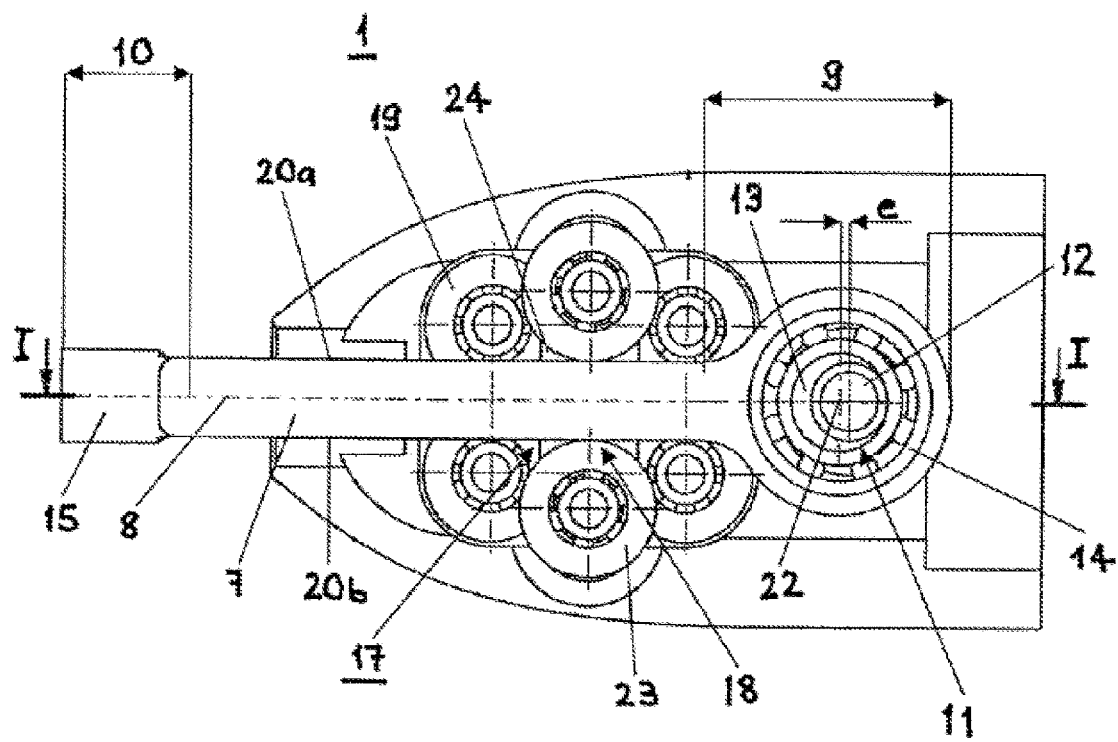

Page 2 device includes second members for a limitation of a movement of the first members, which are movable relative to the housing and which force a movement of the first members transversally to the longitudinal axis of the connecting rod.

11 Claims, 5 Drawing Sheets

(56) References Cited

U.S. PATENT DOCUMENTS

| | | | | | |
|---|---|---|---|---|---|
| 3,642,002 | A | * | 2/1972 | Otterstrom | B23D 51/02 |
| | | | | | 606/177 |
| 3,978,862 | A | * | 9/1976 | Morrison | A61B 17/142 |
| | | | | | 606/174 |
| 4,020,555 | A | * | 5/1977 | Hedrick | B23D 51/10 |
| | | | | | 606/177 |
| 5,201,749 | A | * | 4/1993 | Sachse | A61B 17/144 |
| | | | | | 606/177 |
| 5,916,218 | A | * | 6/1999 | Hagen | B23D 61/123 |
| | | | | | 30/337 |
| 6,007,541 | A | * | 12/1999 | Scott | A61B 17/144 |
| | | | | | 606/177 |
| 7,294,131 | B2 | * | 11/2007 | Kunzler | A61B 17/1671 |
| | | | | | 606/177 |
| 2010/0292701 | A1 | * | 11/2010 | Fisher | A61B 17/142 |
| | | | | | 606/82 |

OTHER PUBLICATIONS

International Preliminary Report Chapter I dated Jan. 26, 2021 issued in corresponding International Patent Application No. PCT/CH2018/000032.

* cited by examiner

SURGICAL SAW APPARATUS

CROSS REFERENCE TO RELATED APPLICATIONS

This application is a U.S. national stage application of PCT/CH2018/000032 filed on Jul. 25, 2018, the contents of which are incorporated herein by reference.

The invention relates to a surgical saw apparatus according to the preamble of patent claim 1.

A surgical saw apparatus comprising a transmission for generating a circular movement of the cutting element, in particular of a sawblade, is known from document DE 10 2009 048 835 A1. By the true circular movement of the sawblade in a plane an optimum protection of soft tissue is achieved. The transmission for generating the circular movement of the sawblade comprises a connecting rod, which is driven by two eccentrics driving the connecting rod synchronously. Herein respectively one driving eccentric is situated in a front section and in a rear section of the connecting rod. The two driving eccentrics are coupled with each other mechanically, for example by means of a gear transmission or a belt drive. This well-known saw apparatus has, however, the disadvantage that the apparatus comprises two synchronously driven eccentrics, which requires the two eccentrics to be coupled mechanically for generating the synchronous rotation movement, which leads to a complex construction of the drive device that drives the connecting rod.

This is to be remedied by the invention. The invention is based on the task to provide a surgical saw apparatus comprising a structurally simple drive device for a connecting rod that executes a circular movement.

The invention solves the given task by a surgical saw apparatus having the features of claim 1.

The advantages obtained by the invention substantially lie in that, due to the surgical saw apparatus according to the invention,

- an exact circular movement of the connecting rod—and thus of the sawblade fixated to the connecting rod—is enabled with only one driven eccentric and a guiding device with a purely translational guidance for the connecting rod relative to two guiding axes which are oriented transversally to each other;
- only one driven eccentric shaft is used, such that a gear transmission or belt drive can be dispensed with, and thus a small overall construction size of the saw apparatus is achievable. This small overall construction size allows a considerable improvement of an application of the saw apparatus. This regards a surgeon's field of vision as well as a freedom of movement, which is in particular relevant for a closed incision guidance (with in-line saw), for example for trepanation cuts of the skull bone, in which a complete piece of bone is removed;
- fewer structural components are needed, which means fewer undercuts and overlapping components (e.g. engaging teeth), such that the saw apparatus is easier and better to clean and thus an increased level of hygiene is achievable;
- the smaller number of structural components also results in reduced maintenance requirements, minimized wear-down and reduced weight, which in turn has a considerable impact on the applicability of the saw apparatus;
- a smaller number of structural components furthermore means a minimized risk of failure of structural components; and
- the saw apparatus can be produced with a smaller manufacturing effort as there are fewer structural components, allowing larger tolerance ranges of the individual parts.

Further advantageous implementations of the invention may be commented as follows:

Protection of soft tissue is generally based on an amplitude, respectively a deflection, of the sawblade which is smaller than the extension of the soft tissue before tearing/cutting. Osseous structures are not capable of giving way like soft tissue can. The soft tissue is ductile and is therefore capable of joining oscillations with a small deflection such that no incision is possible.

If the movement is an elliptic oscillating movement with one center of rotation, there is the problem that an ideal circular movement is realized only in one point. All points towards the eccentric have a smaller abrasion rate than the ideal point all points exceeding the ideal point project farther and farther from the central axis, such that a protection of soft tissue is no longer given from a certain length on.

Studies have shown that in machining processes a large portion of the thermal energy supplied remains with the chips—this is also the case for the bone material that is cut. In a circular movement an optimum removal of chips can be generated as the chips are moved from one sawtooth to the next one and are thus removed from the cutting clearance. An overheating of the bone, which may lead to necrosis, is especially critical. A risk of overheating is considerably reducible by way of the saw apparatus according to the invention.

In one specific embodiment the connecting rod has two side surfaces which extend parallel to a plane, wherein said plane is spanned by the longitudinal axis of the connecting rod and by a bearing axis of the bearing for the eccentric section of the eccentric shaft in the rear section of the connecting rod.

In another embodiment the first members of the guiding device form a linear guidance for the parallel side surfaces of the connecting rod.

Preferably the linear guidance comprises a guiding element or a plurality of guiding elements on each of the two side surfaces of the connecting rod.

In a further embodiment the first members comprise a structural component which is transversally movable relative to the housing, wherein the guiding elements of the linear guidance are arranged on or in said structural component.

Preferentially the second members form a transversal guidance for the structural component relative to the longitudinal axis of the connecting rod.

In another embodiment the eccentric second section of the eccentric shaft has, relative to the first section of the eccentric shaft, an eccentricity e in a range between 0.25 mm and 0.5 mm. Because of this eccentricity e, the most efficient amplitude (diameter of the circular movement) is in a range from 0.5 mm to 1 mm. Due to the parallel-constrained position of the connecting rod, the movement is also circular in further positions, which means that the sawblade moves exclusively in a circular manner in the plane of the connecting rod.

In a further embodiment the drive axle of the drive unit has a rotation speed of at least 9,000 rpm, preferably at least 10,000 rpm.

And in another further embodiment the drive axle of the drive unit has a rotation speed of maximally 22,000 rpm, preferably maximally 20,000 rpm. The high frequency is necessary to enable an acceptable abrasion of osseous structures.

In another embodiment the linear guidance and/or the transversal guidance comprise/comprises two or more roller bearings. This enables achieving the advantage that a friction between the linear guidance and the connecting rod and the transversal guidance for the movable structural component is considerably reducible.

In a further embodiment the surgical saw apparatus furthermore comprises a sawblade.

According to a further aspect of the invention a method for driving a surgical sawblade is provided, the method comprising the following steps:
  a) fixation of a sawblade to a front section of a connecting rod;
  b) rotational driving of an eccentric shaft by means of a drive unit that is connected with a first section of the eccentric shaft;
  c) circular driving of a rear section of a connecting rod by means of an eccentric second section of the eccentric shaft;
  d) guiding the connecting rod in a translational direction that is coaxial with a longitudinal axis of the connecting rod by means of first members, which are movable relative to the housing, for a limitation of the movement of the connecting rod; and
  e) guiding the first members in a translational direction that is transversal to the longitudinal axis of the connecting rod by means of second members, which are movable relative to the housing, for a limitation of the movement of the first members.

In the following the invention and further developments of the invention will be explained in detail making use of the partly schematic illustrations of several exemplary embodiments.

Figure 2:
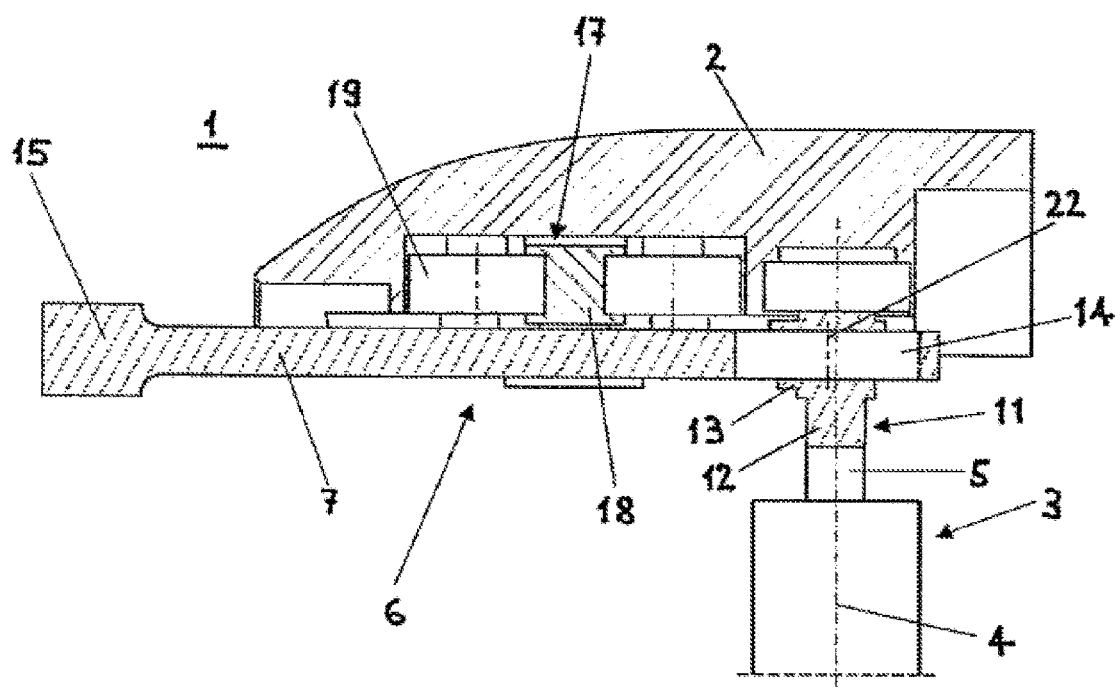
Figure 3:
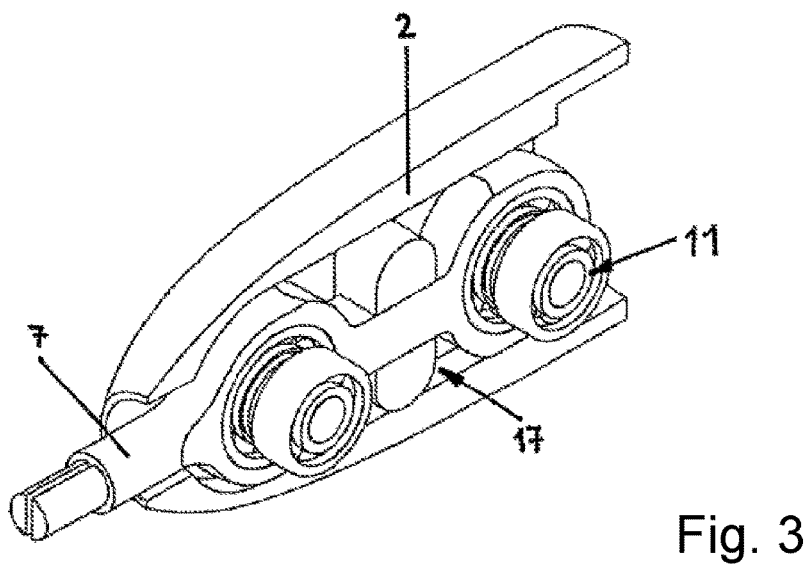
Figure 4:
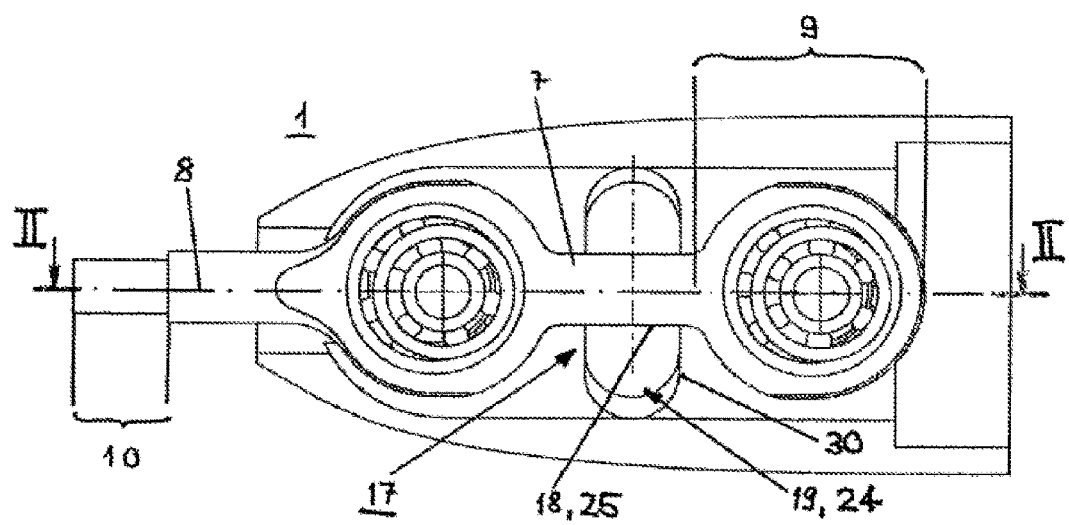
Figure 5:
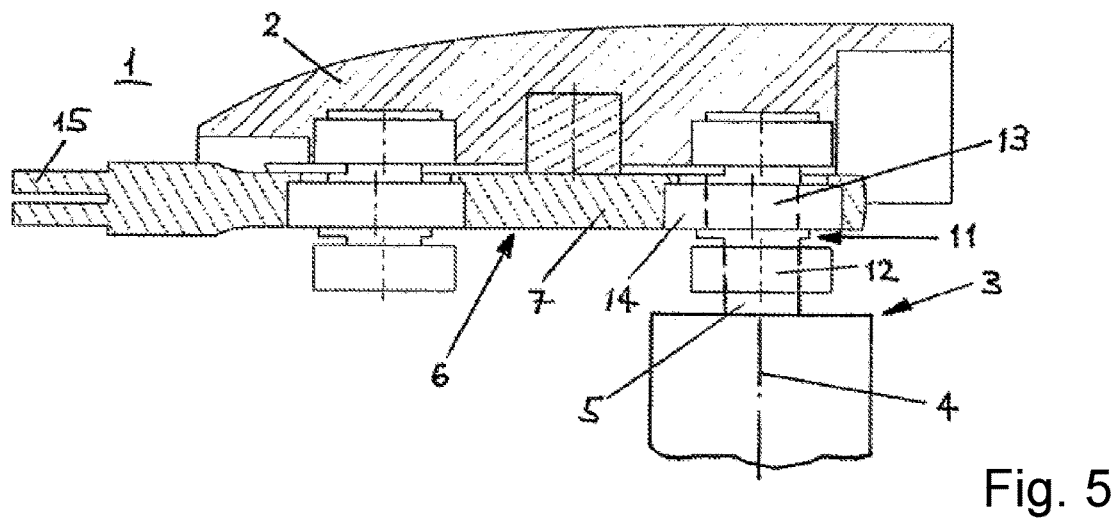
Figure 6:
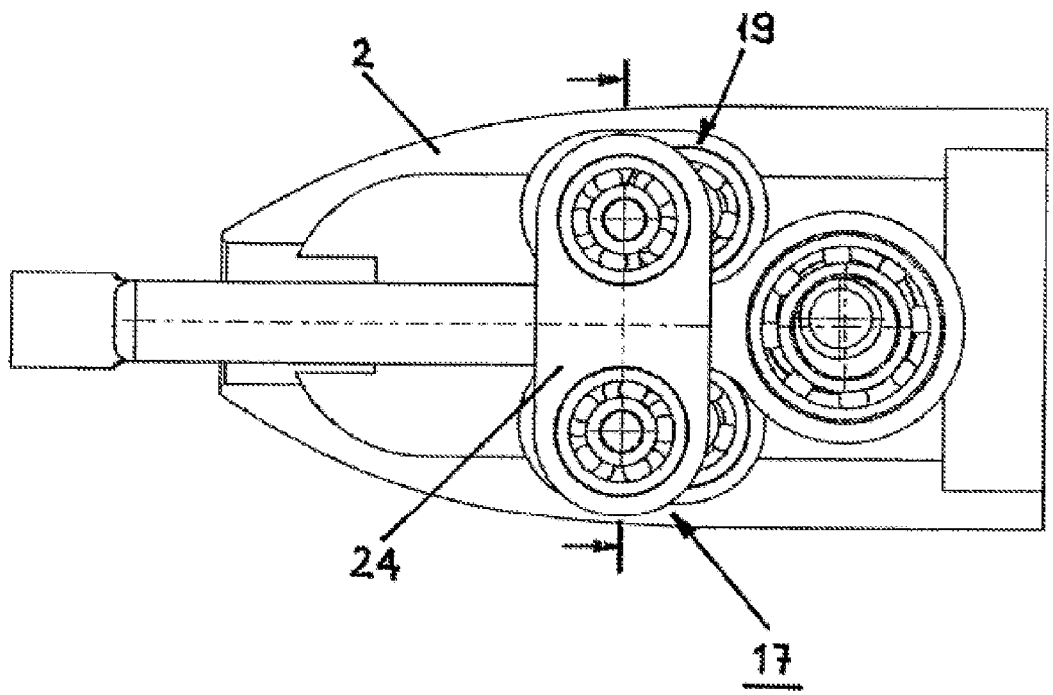
Figure 7:
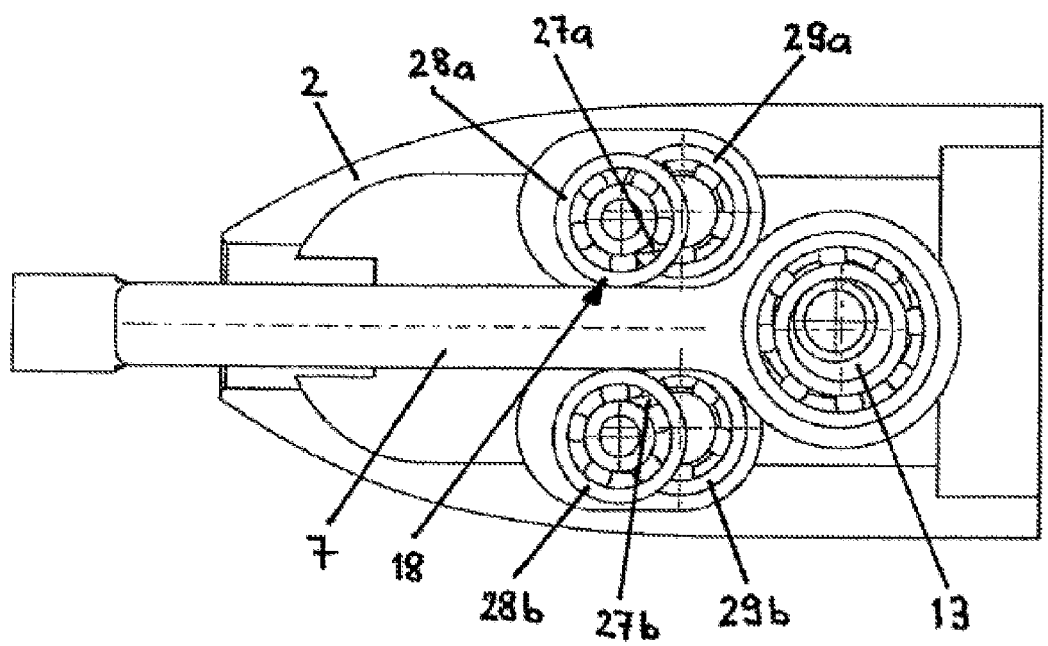
Figure 8:
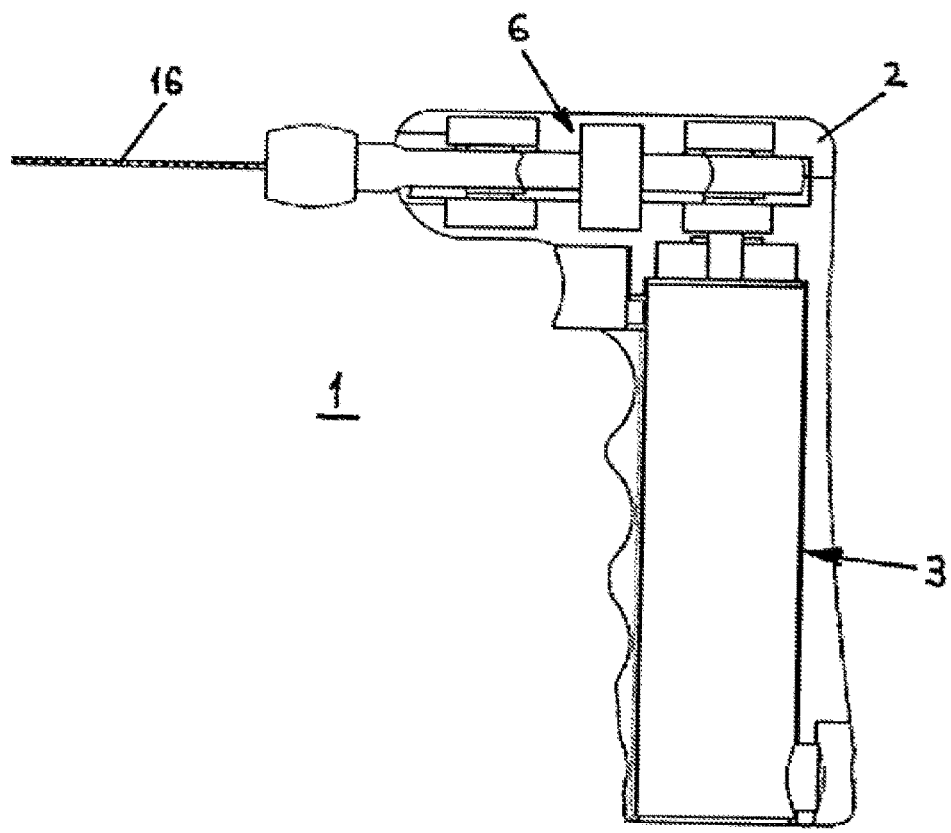
Figure 9:
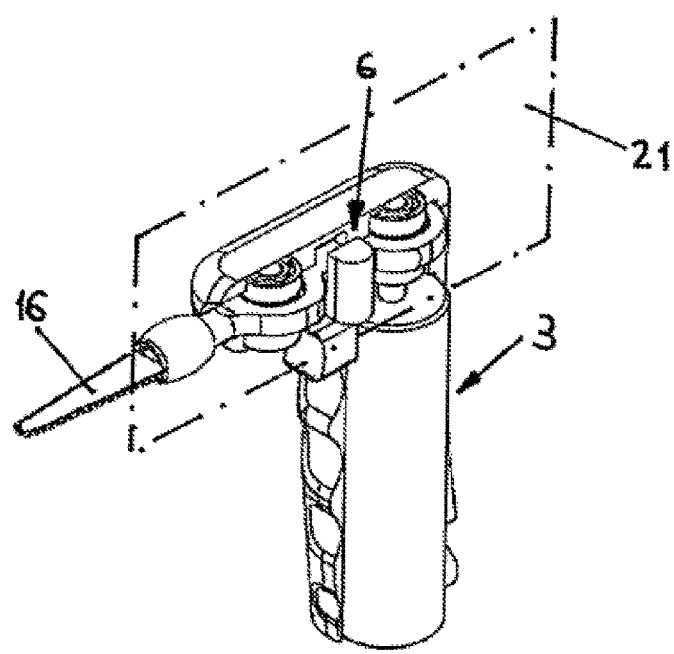
Figure 10:
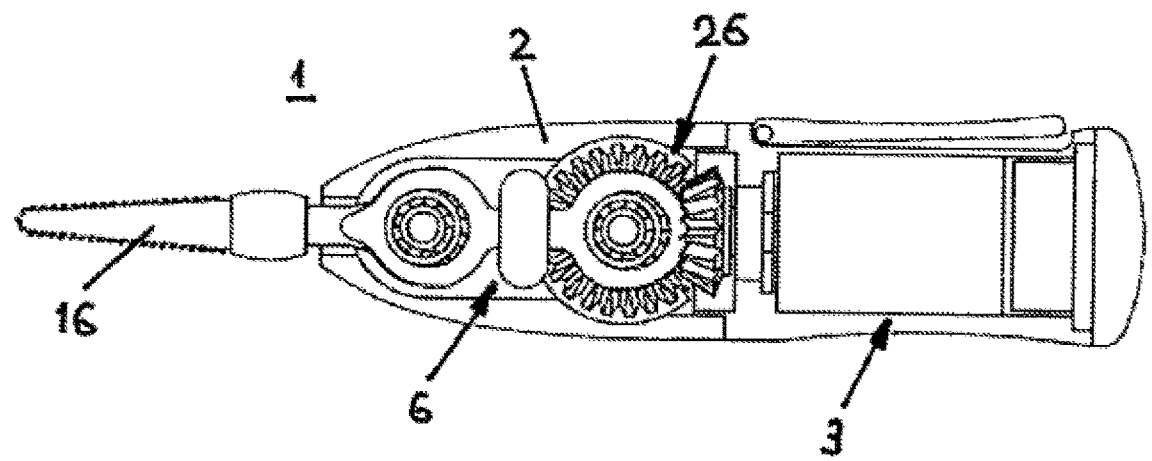
Figure 11:
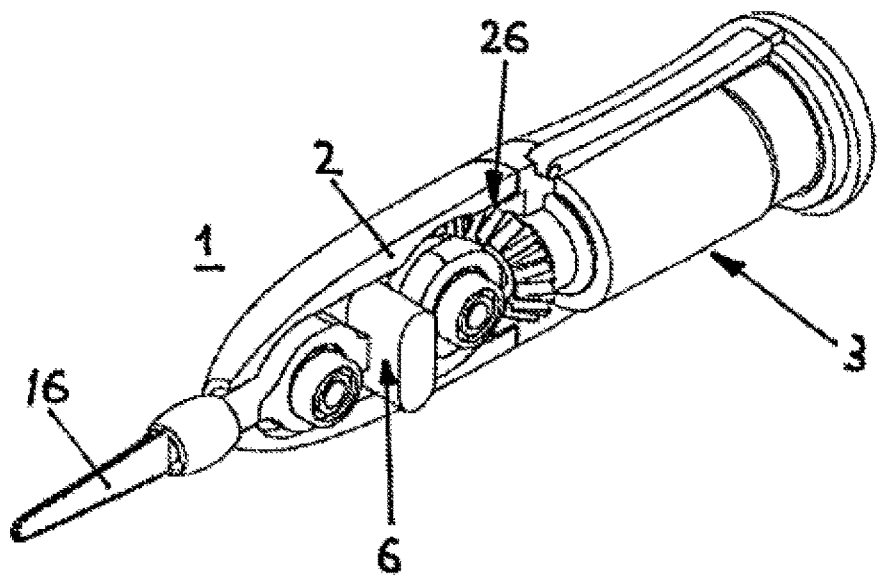

It is shown in:

FIG. 1 a view of a deflection device of a first embodiment of the surgical saw apparatus according to the invention;

FIG. 2 a longitudinal section along line I-1 of the embodiment of the surgical saw apparatus according to the invention that is shown in FIG. 1;

FIG. 3 a perspective view of a longitudinal section of the deflection device of a second embodiment of the surgical saw apparatus according to the invention;

FIG. 4 a view of the deflection device of the embodiment of the surgical saw apparatus according to the invention that is shown in FIG. 3;

FIG. 5 a longitudinal section along line II-II of the embodiment of the surgical saw apparatus according to the invention that is shown in FIG. 3;

FIG. 6 a view of the deflection device of a third embodiment of the surgical saw apparatus according to the invention;

FIG. 7 a partial view of the deflection device of the embodiment of the surgical saw apparatus according to the invention that is shown in FIG. 6;

FIG. 8 a sectional view of the embodiment of the surgical saw apparatus according to the invention that is shown in FIGS. 3 to 5;

FIG. 9 a perspective view of the embodiment of the surgical saw apparatus according to the invention that is shown in FIGS. 3 to 5;

FIG. 10 a sectional view of a further embodiment of the surgical saw apparatus according to the invention, with the deflection device shown in FIGS. 3 to 5; and FIG. 11 a perspective view of the embodiment of the surgical saw apparatus according to the invention that is shown in FIG. 10.

In FIGS. 1 and 2 a first embodiment of the deflection device 6 of the surgical saw apparatus according to the invention 1 is illustrated. Furthermore, to give a better overview, portions of the housing 2 and of the drive unit 3 are shown schematically. The drive unit 3 is integrated in the housing 2 (FIGS. 8 and 9) or fixated on the housing 2 (FIGS. 10 and 11) and comprises a drive axle 5 with a central axis 4, wherein a rotation movement of the drive axle 5 around the central axis 4 can be generated by means of the drive unit 3.

The deflection device 6 shown in FIGS. 1 and 2 substantially comprises a connecting rod 7 which is arranged movably in the housing 2, an eccentric shaft 11 which is connected with the drive axle 5 and the connecting rod 7, and a guiding device 17 for the connecting rod 7. The eccentric shaft 11 comprises a first section 12, which is arranged coaxially with the central axis 4 of the drive axle 5 and is connected with the drive axle 5, and a second section 13, which is arranged eccentrically relative to the first section 12. Herein axes of the first and second sections 12, 13 are arranged in parallel. Herein the eccentric second section 13 has relative to the first section 12 of the eccentric shaft 11 an eccentricity e that is in a range between 0.25 mm and 0.5 mm, depending on an application of the saw apparatus.

The eccentric shaft 11 is supported in the housing 2 concentrically to the first section 12, which is arranged coaxially with the central axis 4 of the drive axle 5, and may comprise a further section that is coaxial with the first section 12, such that it is possible for the eccentric shaft 11 to be supported in a two-part housing 2 at respectively one section that is coaxial with the central axis 4 of the drive axle 5.

The connecting rod 7, which is arranged movably in the housing 2, comprises a longitudinal axis 8, a rear section 9 and a front section 10 with members for a fixation of a sawblade 16. In the rear section 9 of the connecting rod 7 a bearing 14 for the eccentric second section 13 of the eccentric shaft 11 is arranged, which is, to give an example but not limited to this example, implemented as a roller bearing. Alternatively the bearing 14 could also be implemented as a slide bearing. The front section 10 of the connecting rod 7 comprises a fixation device 15 for the sawblade 16.

The guiding device 17 for the connecting rod 7 serves for a transformation of the circular movement, which is exerted onto the bearing 14 in the rear section 9 by the eccentric second section 13 of the eccentric shaft 11, into a combined translational movement of the connecting rod 7 in two mutually orthogonal axial directions.

The guiding device 17 comprises first members 18, which are movable relative to the housing 2, for a limitation of the movement of the connecting rod 7, and second members 19, which are movable relative to the housing 2 and which limit the movement of the first members 18. By means of the first members 18, a translational movement of the connecting rod 7 coaxially with the longitudinal axis 8 of the connecting rod 7 is forced, while a movement of the first members 18 transversally to the longitudinal axis 8 of the connecting rod 7 is forced by the second members 19. The connecting rod 7 therefore moves coaxially with its longitudinal axis 8 and at the same time in a transversal direction orthogonally to the longitudinal axis 8, wherein the longitudinal axis 8 of the connecting rod 7 is translated in parallel. As a result, the circular movement of the bearing 14 in the rear section 9 of the connecting rod 7 is transferred to the front section 10 and thus to the sawblade 16.

The connecting rod 7 comprises two side surfaces 20*a*, 20*b* extending parallel to a plane 21, said plane 21 being spanned by the longitudinal axis 8 of the connecting rod 7 and by the bearing axis 22 of the bearing 14 for the eccentric section 13 of the eccentric shaft 11 in the rear section 9 of the connecting rod 7. The first members 18 of the guiding device 17 are implemented as a linear guidance for the parallel side surfaces 20*a*, 20*b* of the connecting rod 7 and respectively comprise one or a plurality of guiding element/s 23 which are adjacent to each of the two side surfaces 20*a*, 20*b* of the connecting rod 7.

The first members 18 comprise a structural component 24, which is movable transversally to the housing 2, wherein the guiding elements 23 of the linear guidance are arranged on said structural component 24. The guiding elements 23 of the first members 18 are, to give an example but not limited to this example, embodied as roller bearings which are fixated on the structural component 24 that is movable transversally to the longitudinal axis 8 of the connecting rod 7. The linear guidance is thus realized by the roller bearings which are fixated on the structural component 24.

The second members 19 form a transversal guidance for the structural component 24 relative to the longitudinal axis 8 of the connecting rod 7. Furthermore the transversal guidance comprises, by way of example and not limited thereto, roller bearings 26, which are fixated in the housing 2 so as to enable a movement of the structural component 24 orthogonally to the longitudinal axis 8 of the connecting rod 7.

The embodiment of the surgical saw apparatus 1 that is illustrated in FIGS. 3 to 5 differs from the embodiment illustrated in FIGS. 1 and 2 only in that the connecting rod 7 is guided in a groove 25 in the structural component 24, that the structural component 24, which is movable transversally to the longitudinal axis 8 of the connecting rod 7, is guided slidably in a further groove 30 that is arranged in the housing 2 orthogonally to the longitudinal axis 8 of the connecting rod 7, and that the connecting rod 7 is supported on a passive second eccentric shaft 11' in a section that is situated between the front section 9 and the rear section 10. This passive eccentric shaft 11' is not driven by the drive unit 3.

An overall illustration of the embodiment of the surgical saw apparatus 1 according to FIGS. 3 to 5 is given in FIGS. 8 and 9. The housing 2 is embodied in a two-part implementation, with the housing portion containing the drive unit 3 being realized as a handle and extending in the direction of the central axis 4 of the drive axle 5. The drive unit 3 may, to give an example but not limited to this example, comprise an electromotor and operating elements.

The sawblade 16 is implemented longitudinally and may have a length between 15 mm and 100 mm, depending on the application of the saw apparatus 1. Furthermore the sawblade 16 may have parallel sides in its longitudinal direction or may taper towards the free end of the sawblade 16. The sawteeth are arranged on both longitudinal sides and at the free end of the sawblade 16, wherein on the toothed circumferential section of the sawblade 16, analogously to a chainsaw, the cutting sides of the sawteeth point in the same direction.

A further overall illustration of a further embodiment of the surgical saw apparatus 1 is given in FIGS. 10 and 11. The embodiment illustrated in FIGS. 10 and 11 differs from the embodiment given in FIGS. 8 and 9 only in that the drive unit 3 is arranged in such a way that the central axis 4 of the drive axle 5 is situated in the plane spanned by the longitudinal axis 8 of the connecting rod 7 which is moved in a longitudinal and in a transversal direction, and extends, depending on a situation of the connecting rod 7, coaxially with or parallel to the longitudinal axis 8 of the connecting rod 7 and that, between the drive axle 5 and the eccentric shaft 11, a gear transmission 26 is arranged, by means of which the rotation movement of the drive axle 5 is deflected into the rotation movement of the eccentric shaft 11 that is angled by 90°.

The construction forms (in-line and pistol handle) presented in FIGS. 8 to 11 are configured for different applications, for the purpose of allowing the operator an ideal handling, body posture, patient positioning, field of vision, force input, etc.

The embodiment of the surgical saw apparatus 1 illustrated in FIGS. 6 and 7 differs from the embodiment illustrated in FIGS. 1 and 2 only in that the structural component 24 of the first members 18 of the guiding device 17 is supported on the housing 2 such that it is pivotable by two levers 27*a*, 27*b*, which are rotatably connected with the housing 2. The structural component 24, the two levers 27*a*, 27*b* which are rotatably supported on the structural component 24 via first articulations 28*a*, 28*b*, and the housing section between the two second articulations 29*a*, 29*b* for the levers 27*a*, 27*b*, which are arranged on the housing 2, form a parallelogram whose sides are rotatable against each other around the first, respectively second articulations 28*a*, 28*b*, 29*a*, 29*b*. The first and second articulations 28*a*, 28*b*, 29*a*, 29*b*, to give an example but not limited to this example, comprise roller bearings. Alternatively slide bearings could as well be present instead of roller bearings.

Although, as has been described above, there are different embodiments of the present invention, these are to be understood such that the different features may be used both individually and in any arbitrary combination.

The present invention is therefore not just limited to the particularly preferred embodiments which are given above.

The invention claimed is:

1. A surgical saw apparatus, comprising:
   A) a housing;
   B) a drive unit with a drive axle comprising a central axis, wherein a rotation movement of the drive axle around the central axis can be generated by means of the drive unit;
   C) a deflection device, comprising:
      C1) a connecting rod that is arranged movably in the housing, with a longitudinal axis, with a rear section and with a front section;
      C2) an eccentric shaft with at least one first section, which is arranged coaxially with the central axis of the drive axle and is connected with the drive axle, and with a second section which is eccentric relative to the first section, wherein the rear section of the connecting rod comprises a bearing for the eccentric second section of the eccentric shaft, and the front section of the connecting rod comprises a fixation device for a sawblade;
      C3) a guiding device for the connecting rod,
   wherein
   D) the guiding device comprises first members for a limitation of a movement of the connecting rod, which are movable relative to the housing and which force a translational movement of the connecting rod coaxially with the longitudinal axis of the connecting rod, and E) the guiding device comprises second members for a limitation of a movement of the first members, which are movable relative to the housing and which force a movement of the first members transversally to the longitudinal axis of the connecting rod, wherein the first members of the guiding device form a linear guidance for the parallel side surfaces of the connecting rod.

2. The surgical saw apparatus according to claim 1, wherein the connecting rod comprises two side surfaces extending parallel to a plane, said plane being spanned by the longitudinal axis of the connecting rod and by a bearing axis of the bearing for the eccentric section of the eccentric shaft in the rear section of the connecting rod.

3. The surgical saw apparatus according to claim 1, wherein the linear guidance comprises one guiding element or a plurality of guiding elements on each of the two side surfaces of the connecting rod.

4. The surgical saw apparatus according to claim 1, wherein the first members comprise a structural component, which is movable transversally to the housing, wherein the guiding elements of the linear guidance are arranged on or in said structural component.

5. The surgical saw apparatus according to claim 1, wherein the second members form a transversal guidance for the structural component relative to the longitudinal axis of the connecting rod.

6. The surgical saw apparatus according to claim 1, wherein the eccentric second section has, relative to the first section of the eccentric shaft, an eccentricity e in a range between 0.25 mm and 0.5 mm.

7. The surgical saw apparatus according to claim 1, wherein the drive axle of the drive unit has a rotation speed of at least 9,000 rpm, preferably at least 10,000 rpm.

8. The surgical saw apparatus according to claim 1, wherein the drive axle of the drive unit has a rotation speed of maximally 22,000.

9. The surgical saw apparatus according to claim 1, wherein the linear guidance and/or the transversal guidance comprise/comprises two or more roller bearings.

10. The surgical saw apparatus according to claim 1, wherein the surgical saw apparatus further comprises a sawblade.

11. The surgical saw apparatus according to claim 1, wherein the drive axle of the drive unit has a rotation speed of maximally 20,000 rpm.

* * * * *